(12) United States Patent
Windhorst et al.

(10) Patent No.: US 8,921,618 B2
(45) Date of Patent: Dec. 30, 2014

(54) RECOVERY OF TRIMETHYLOLPROPANE FROM PURIFICATION RESIDUE

(71) Applicants: Kenneth A. Windhorst, Portland, TX (US); Oakley T. Cortez, Corpus Christi, TX (US); Donald K. Raff, Waynesville, NC (US)

(72) Inventors: Kenneth A. Windhorst, Portland, TX (US); Oakley T. Cortez, Corpus Christi, TX (US); Donald K. Raff, Waynesville, NC (US)

(73) Assignee: OXEA Bishop LLC, Dallas, TX (US)

( * ) Notice: Subject to any disclaimer, the term of this patent is extended or adjusted under 35 U.S.C. 154(b) by 355 days.

(21) Appl. No.: 13/621,345

(22) Filed: Sep. 17, 2012

(65) Prior Publication Data

US 2014/0081052 A1 Mar. 20, 2014

(51) Int. Cl.
*C07C 27/26* (2006.01)

(52) U.S. Cl.
USPC .......................................................... 568/868

(58) Field of Classification Search
USPC ........................................................... 566/868
See application file for complete search history.

(56) References Cited

U.S. PATENT DOCUMENTS

| | | |
|---|---|---|
| 5,603,835 A | 2/1997 | Cheung et al. |
| 5,948,943 A | 9/1999 | Supplee et al. |
| 6,096,905 A | 8/2000 | Supplee et al. |
| 6,265,623 B1 | 7/2001 | Morawietz et al. |
| 6,316,679 B1 | 11/2001 | Supplee et al. |
| 7,301,058 B2 | 11/2007 | Wartini et al. |
| 2002/0033325 A1 | 3/2002 | Ninomiya et al. |
| 2003/0088131 A1* | 5/2003 | Dernbach et al. ............. 568/884 |

FOREIGN PATENT DOCUMENTS

| | | |
|---|---|---|
| DE | 287251 | 2/1991 |
| DE | 287252 A5 | 2/1991 |
| DE | 102010033844 | 2/2012 |
| WO | 97-01523 | 1/1997 |
| WO | 0147848 A1 | 7/2001 |

OTHER PUBLICATIONS

International Search Report and Written Opinion, Oct. 28, 2013.

* cited by examiner

*Primary Examiner* — Sudhakar Katakam
*Assistant Examiner* — Kofi Adzamli
(74) *Attorney, Agent, or Firm* — Michael W. Ferrell

(57) ABSTRACT

A method of reclaiming trimethylolpropane from purification residue includes hydrolyzing a purification residue with an aqueous medium in the presence of (i) an acid and (ii) an oxidizing agent. The method is particularly effective to reclaim trimethylolpropane from monolinear-bis-TMP-formal:

monolinear bis-TMP-formal (MBLF or TMP-BMLF); Formula II:

$$[C_2H_5C(CH_2OH)_2CH_2O]_2CH_2 \qquad (II).$$

18 Claims, 3 Drawing Sheets

RECOVERY OF TRIMETHYLOLPROPANE FROM PURIFICATION RESIDUE

CROSS REFERENCE TO RELATED APPLICATION

This application relates to the subject matter of U.S. patent application Ser. No. 13/621,494, now U.S. Pat. No. 8,759,593, entitled RECOVERY OF ALCOHOLS FROM PURIFICATION RESIDUE filed of even date herewith.

TECHNICAL FIELD

The present invention relates to improved recovery of trimethylolpropane (TMP) from purification residue including TMP-formals by way of acidic hydrolysis in the presence of an oxidizing agent.

BACKGROUND

TMP is prepared from n-butyraldehyde and formaldehyde. In one preferred process, base-catalyzed aldol reaction initially generates 2,2-dimethylolbutyraldehyde in a first reaction step which is then converted to a TMP-formate mixture by way of a Cannizzaro reaction. The TMP-containing mixture is typically extracted with an organic solvent, such as ethyl acetate providing an aqueous phase containing the formate and the organic phase comprising TMP. The solvent is separated and the crude TMP is purified by distillation. Typical processing is seen in U.S. Pat. No. 5,603,835 to Cheung et al., Comparative Example 1, Col. 7. See, also, U.S. Pat. No. 5,948,943 to Supplee et al.

Purification residue of the TMP production process includes various formals in which TMP equivalents are chemically bound. Such formals may include all or some of the following:

monocyclic TMP-formal (MCF); Formula I:

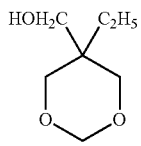

(I)

monolinear bis-TMP-formal (MBLF or TMP-BMLF); Formula II:

(II)

Methyl-(monolinear)TMP-formal; Formula III

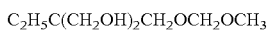

(III)

Methyl-(bislinear)TMP-formal; Formula IV

(IV)

Also, typically present in the purification residue are substantial amounts of di-TMP and the cyclic formal of di-TMP; Formula V:

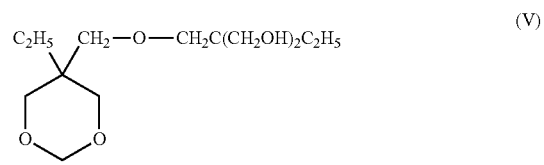

(V)

as well as relatively large amounts of TMP. TMP has a structural formula:

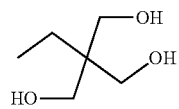

2-(hydroxymethyl)-2-ethylpropane-1,3-diol and di-TMP has a structural formula:

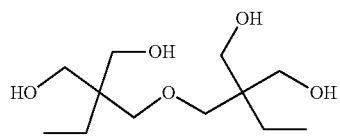

2-[2,2-bis(hydroxymethyl)butoxymethyl]-2-ethylpropane-1,3-diol

In many cases, the main components in the purification residue are TMP, di-TMP and linear bis-TMP-formal (MBLF) (Formula II). Cyclic formals are usually present in smaller amounts.

Because the residues contain substantial amounts of TMP, either physically mixed or bound in formal equivalents, and also di-TMP, which is also a valuable product for resins, lubricant oils or the like, various processes to recover TMP and di-TMP from residues have been developed.

U.S. Pat. No. 7,301,058 to Wartini et al. discloses a process for recovering TMP from purification residue using acid treatment in water. Increases in TMP levels of from −6.4% to 36.3% are reported in Table 1, Col. 9. DD 28 72 51 likewise refers to cleavage of TMP formals under acidic conditions followed by thermal treatment.

U.S. Pat. No. 6,265,623 to Moraweitz et al. relates to the reductive cleavage of linear and cyclic acetals, especially formals, in an aqueous medium containing a formate which takes place by hydrogenation with hydrogen in the presence of a heterogeneous hydrogenation catalyst at a pH value of less than 7 at a temperature of over 200° C. See, also, WO 97/01523. Under these reaction conditions, formaldehyde liberated from the formals is hydrogenated to methanol. A similar hydrogenation process of the TMP residue is disclosed in DE 10 2010 033 844. The aqueous solution from the hydrogenation step is freed from the catalyst and other solids and then treated with ion exchangers. From the collected solution, light ends are removed and then a TMP-enriched head fraction is recovered.

United States Patent Application Publication No. US 2002/0033325 of Ninomiya et al. teaches to add an acid to TMP purification residue and to add a scavenger for the formaldehyde liberated in the acid treatment. Said scavenger, such as hydroxylamine salts, avoids the formation of cyclic formals, such as the cyclic formal of TMP and the cyclic formal of di-TMP.

In U.S. Pat. No. 6,316,679 to Supplee et al. there is disclosed a process for treating TMP heavy ends residue with a strong acid in the presence of an alcohol formaldehyde scavenger. Increases in TMP content from 10% to 30% are reported. See Table III, Col. 6. Similar features appear in U.S. Pat. No. 6,096,905, also to Supplee et al.

SUMMARY OF INVENTION

We have found that unexpectedly high yield of TMP from conversion of TMP-formals is achieved by treatment of TMP purification residue with an acid in the presence of an oxidizing agent. Without intending to be bound by any particular theory, it is believed the oxidizing agent inhibits or prevents cyclization of formals. The formaldehyde liberated in the cleavage of the TMP-formals is oxidized to formic acid and the concurrent formation of cyclic formals of TMP is substantially reduced or eliminated. In consequence, the efficiency of the TMP production process can be substantially improved. Typically, a two-step process is employed which converts TMP bis linear formal (MBLF) to TMP and potassium formate:

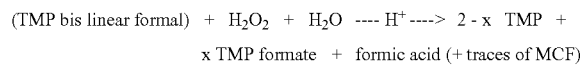

and:

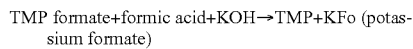

KFo is extracted away from the TMP using an ethyl acetate multistage extraction process in a preferred embodiment.

Preferred acids include strong mineral acids such as sulfuric acid, phosphoric acid, hydrochloric acid, sulfonic acid and the like or organic acids, such as formic acid, acetic acid, or oxalic acid. Preferably formic acid or an acid-functional ion exchange resin is selected. Particularly preferred are sulfonic acid functional ion exchange resins. The acidic compound is added to the aqueous medium in an amount such that the pH value is usually less than 4, typically in the range of from 1 to 4 and in particular in the range of from 1.5 to 3.

As oxidation reagent oxygen gas, ozone, oxygen containing gas, ozone containing gas, peracids such as peracetic acid or aqueous hydrogen peroxide and the like can be used. Preference is given to an aqueous hydrogen peroxide solution. Hydrogen peroxide will be reduced to water and no additional component will be formed during this oxidizing treatment.

The inventive method provides a simple and cost-saving process to improve the overall TMP efficiency. The prior art teaches in some aspects hydrogenation in the presence of a hydrogenation catalyst which makes the known process more complicated and requires additional catalytic material including its handling. Further, the use of various scavengers as known in the art adds an additional auxiliary component, which reaction product from the formaldehyde scavenging process has to be separated.

Using an oxidizing reagent has the advantage that formaldehyde liberated will be oxidized to formic acid which can be converted into alkali or alkaline earth metal formate after neutralization of the treated purification residue with an aqueous solution of said metal compounds. The recovered aqueous formate solution can be combined with process streams if the reaction of n-butyraldehyde with formaldehyde is carried out as an inorganic Cannizzaro process which produces formates. In any event, the inventive method can optionally be applied for heavies from any TMP production process, such as a process for making TMP by way of reacting butyraldehyde with formaldehyde followed by hydrogenation as described in U.S. Pat. No. 7,301,058 to Wartini et al. noted above, the disclosure of which is incorporated herein by reference. Likewise, other formals and acetals can be recovered by way of the inventive process as described hereinafter.

Further details and advantages will become apparent from the discussion which follows.

DESCRIPTION OF DRAWINGS

The invention is described in detail below in connection with numerous examples and in connection with the attached Figures. In the Figures.

DETAILED DESCRIPTION

Figure 1:
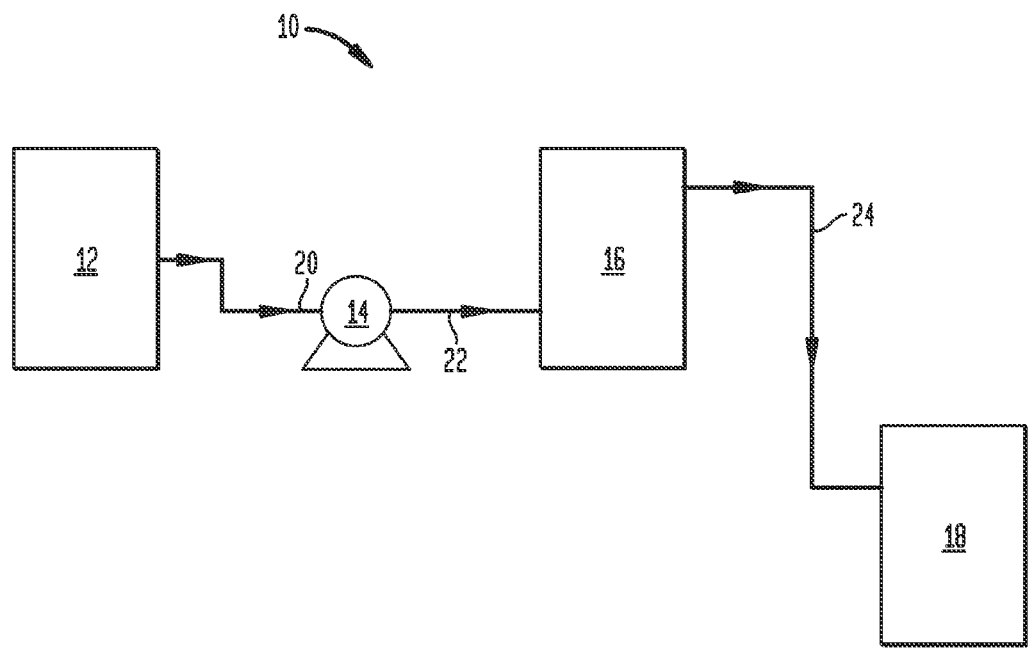
FIG. 1 is a schematic diagram illustrating continuous operation of a reactor recovering polyols from purification residue in accordance with the invention.

The invention is described in detail below in connection with the Figures for purposes of illustration, only. The invention is defined in the appended claims. Terminology used throughout the specification and claims herein is given its ordinary meaning as supplemented by the discussion immediately below, for example, "conversion", "selectivity" and yield are related by the mathematical definition X(conversion)*S(selectivity)=Y(yield), all calculated on a weight or molar basis; e.g. in a certain reaction, 90% of substance A is converted (consumed), but only 80% of it is converted to the desired substance B and 20% to undesired by-products, so conversion of A is 90%, selectivity for B 80% and yield of substance B is 72% (=90%*80%).

For purposes of calculating weight ratios or percentages, "Organic", "organic mixture" and like terminology refers to the subject composition or component on a dry basis unless the context indicates otherwise.

Unless otherwise indicated, "percent", "%" or like terminology refers to weight percent of a component. Likewise, "parts" refers to parts by weight unless otherwise indicated.

Residence time in a continuous reactor is calculated as the steady state or average volume of the reaction medium in the reactor divided by the volumetric flow rate through the reactor.

Reaction rates and yields are especially favorable with respect to linear formal residues of TMP as described below.

Examples 1-5

TMP was prepared from n-butyraldehyde and formaldehyde by way of a base-catalyzed aldol reaction initially generating 2,2-dimethylolbutyraldehyde in a first reaction step which was then converted to a TMP and TMP-formate mixture by way of a Cannizzaro reaction. The TMP-containing mixture was extracted with ethyl acetate providing an aqueous phase containing the formate and the organic phase comprising TMP. The solvent was separated and the crude TMP was purified by distillation as described generally in U.S. Pat. No. 5,603,835 to Cheung et al., Comparative Example 1, Col. 7. The distillation (purification) residue or "heavies" was used as feed to the inventive process. In Tables 1 and 2, the heavies are referred to as starting materials and analyses are provided on a dry basis for the purification residues and the products, excluding water, oxidizing agent, and acid which concentrations are reported on a wet basis as present in the aqueous reaction mixture in Tables 1 and 2.

The procedure followed for Examples 1-5 was to mix about 65 grams of TMP heavies (analyses as per Tables 1, 2) with from about 130 to 260 grams of water (2/1 up to 4/1 water to organics ratio), from about 8 to about 20 grams of formic acid (sometimes referred to herein as Hfo or HFO) or a corresponding amount of sulfonic acid resin, from about 7 to about 20 grams of hydrogen peroxide (100% basis, reported wet in Tables 1 and 2). Anywhere from 3% $H_2O_2$ up to 30% based on the dry weight of starting material has little effect on the process. The water in the $H_2O_2$ solution is included in the water added and included in the percentage of acid and $H_2O_2$ in Tables 1 and 2. The reaction mixture was shaken to make it homogenous and then heated to 70° C. to 90° C. for various lengths of time (2-4 hours) to achieve conversion of MBLF. The aqueous medium is optionally neutralized with potassium hydroxide to provide potassium formate which may be combined with formate generated in the Cannizzaro synthesis, as noted above, after further work-up. Details and results appear in Tables 1, 2 below.

Further work-up includes extracting formates from the reclaimed TMP and distillation of the TMP to purified form as is known in the art.

TABLE 1

| Component | Starting Material | Example 1 Treated 1% $H_2O_2$ + 4% Hfo | Example 2 Treated and Neutralized 1% $H_2O_2$ + 4% Hfo Neutralized, pH = 9+ | Example 3 Treated % $H_2O_2$ + 6% A16 resin** |
|---|---|---|---|---|
| % MCF | 0 | 3.5 | 3.51 | 11.51 |
| % TMP | 15.66 | 46.88 | 55.84 | 54.13 |
| % TMP formates | 0 | 14.1 | 3.77 | 5.7 |
| % DMB* | 5.56 | 7.44 | 8.87 | 8.79 |
| % Di TMP | 15.26 | 9.39 | 12.65 | 11.49 |
| % MBLF | 54.15 | 4.19 | 5.39 | 0.08 |
| Unknowns | 9.37 | 14.5 | 9.97 | 8.3 |
|  |  |  |  | pH = 2.6 |
| MBLF Conversion |  | 92.26 | 90.05 | 99.85 |
| TMP yield (weight) | #TMP/#MBLF consumed | 0.62 | 0.82 | 0.71 |
| MCF yield (weight) | #MCF/#MBLF consumed | 0.07 | 0.07 | 0.21 |
| % molar TMP selectivity from MBLF |  | 65.29 | 86.09 | 74.33 |

*dimethylolbutyraldehyde
**sulfonic acid functional macroreticular ion exchange resin

TABLE 2

| Component | Starting Material | Example 4 Treated 2% $H_2O_2$ + 4% Hfo | Example 5 Treated and Neutralized 2% $H_2O_2$ + 4% Hfo Neutralized (longer) |
|---|---|---|---|
| % MCF | 0 | 3.97 | 3.81 |
| % TMP | 11.07 | 56.91 | 63.22 |
| % TMP formates | 0 | 12.7 | 2.87 |
| % DMB | 5.9 | 5.98 | 7.27 |
| % Di TMP | 15.05 | 10.49 | 13.33 |
| % MBLF | 58.97 | 0.37 | 0.49 |
| Unknowns | 9.01 | 9.58 | 9.01 |
| MBLF Conversion |  | 99.37 | 99.17 |
| TMP yield (Weight) | #TMP/#MBLF consumed | 0.78 | 0.89 |
| MCF yield (weight) | #MCF/#MBLF consumed | 0.07 | 0.07 |
| % molar TMP yield from MBLF |  | 81.73 | 93.17 |

Examples 6-13

Additional trials were carried out in an apparatus 10 shown schematically in FIG. 1. The reaction system included a stirred vessel 12, a pump 14, a heated overflow, continuous (plug flow type) reactor 16 and a collection vessel 18. In operation, starting material having the composition generally as in Examples 2, 4 and 5 was charged to stirred vessel 12, along with water, formic acid and hydrogen peroxide, in amounts as in Examples 1-5. The reactants were homogenized in stirred vessel 12 and continuously fed to reactor 16 via lines 20, 22 and pump 14 wherein the reactants were maintained at reaction temperature for a residence time duration of 2-6 hours. Overflow from reactor 16 after the aforementioned residence time in the reactor was continuously collected in vessel 18 by way of line 24. The material was neutralized as noted in Examples 2, 4 and 5 and analyzed for conversion of MBLF to TMP. The effects of temperature and reaction time on MBLF conversion to TMP appear in Table 3.

TABLE 3

Reaction Time, Temperature Results

| Reactor Temperature ° C. | Reactor Residence Time, Hours | MBLF Conversion (wt. %) |
|---|---|---|
| 60 | 2 | 7% |
|    | 4 | 15% |
|    | 6 | 21% |
| 75 | 2 | 39% |
|    | 4 | 61% |
|    | 6 | 74% |
| 90 | 2 | 92% |
|    | 4 | 97% |

Suitable and preferred process features are listed in Table 4 below.

TABLE 4

Process Features

| Process Feature | Typical Range(s) | Preferred Range(s) |
|---|---|---|
| Hydrolysis Temperature ° C. | 50° C.-99° C. | 70° C.-95° C. |
| Reaction Time; Residence Time in Reactor under Reaction Conditions, hours | 0.5-10<br>1-7.5 | 1.5-4.5 |
| Oxidizing Agent; % by Weight Based on Dry Starting Material | 2%-40%<br>4%-20% | 5%-10% |
| Acid Concentration; % by Weight of Hydrolysis Medium Wet Basis | 0.5%-20%<br>1%-15% | 2%-10% |
| pH of Reaction Medium Prior to Neutralization | less than 4<br>1 to 4 | 1.5 to 3 |
| Water/Organic Ratio W/W | 0.5 to 4<br>1-3 | 1.5 to 2.5 |
| Yield, Weight Basis; Weight of polyhydric alcohol reclaimed per weight of polyhydric alcohol derivate in feed, % | 50%-99%<br>60%-98% | 75%-95%<br>>80% |

Example 14

Integration with Conventional TMP Recovery

Figure 2:
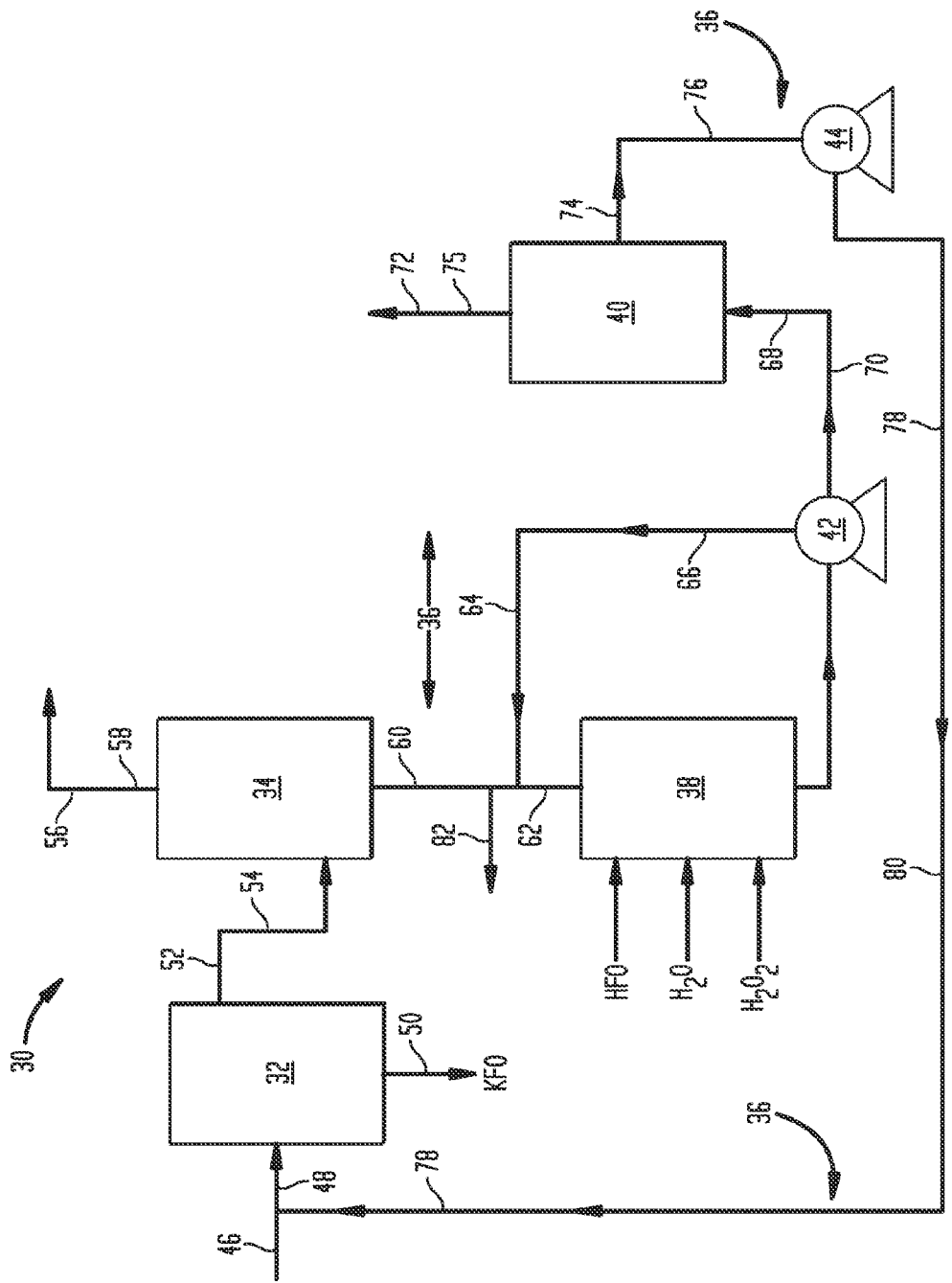
FIG. 2 is a simplified schematic diagram of a polyol reclamation system of the invention integrated with a conventional product recovery system.

The process of the present invention may be integrated into an existing TMP recovery process as shown schematically in the apparatus of FIG. 2.

FIG. 2 shows an apparatus 30 including a multistage water/ethyl acetate extraction system 32, a distillation tower 34 and a residue recovery recycle loop 36. Loop 36 includes a mixing system 38, a heated hydrolysis reactor 40, as well as pumps 42, 44 and a plurality of connecting conduits therebetween.

Extraction system 32 and purification tower 34 may be of conventional design wherein a TMP/formate crude product stream 46 is fed to system 32 via line 48 where potassium formate is extracted in an aqueous phase and recovered as stream 50. TMP is recovered from system 32 in an organic phase 52 and fed to tower 34 via line 54 wherein TMP is taken together with light ends as an overhead stream 56 via line 58 and directed to further purification (not shown).

Distillation residue exits tower 34 as stream 60 and is fed to mixing system 38 via line 62. In mixing system 38 hydrogen peroxide, water and formic acid are added to the purification residue and the resulting mixture is partially recycled to system 38 as stream 64 via line 66 by way of pump 42. Any equivalent means of providing hydrogen peroxide, water and acid to the reaction mixture are also contemplated, for example, these components may be admixed before or provided directly to reactor 40.

Pump 42 also provides a reactant stream 68 including purification residue, formic acid and hydrogen peroxide to hydrolysis and oxidation reactor 40 via line 70. In reactor 40, TMP is recovered from stream 68 as described above in connection with Examples 1-13 and any excess $H_2O_2$ is vented to a scrubber as stream 72 via line 75.

Reactor 40 is a plug flow type overflow reactor. A reacted stream 74 is enriched in TMP by the alcohol recovery process of the invention and the liquor exits via line 76 to pump 44 which pumps the material as stream 78 via line 80 to feed line 48 where it is recycled to extraction system 32.

The alcohol reclaimed from the purification residue is thus returned to an existing purification system where it is recovered along with product from a fresh raw product stream. If so desired, one could treat and recycle recovered material directly to purification tower 34.

As system 30 operates, levels of heavy by-products in stream 60 increase because of the operation of residue cycle loop 36. A purge stream 82 is withdrawn from stream 60 and may be further processed or incinerated for steam generation.

Example 15

Integration with Existing TMP Distillation

Figure 3:
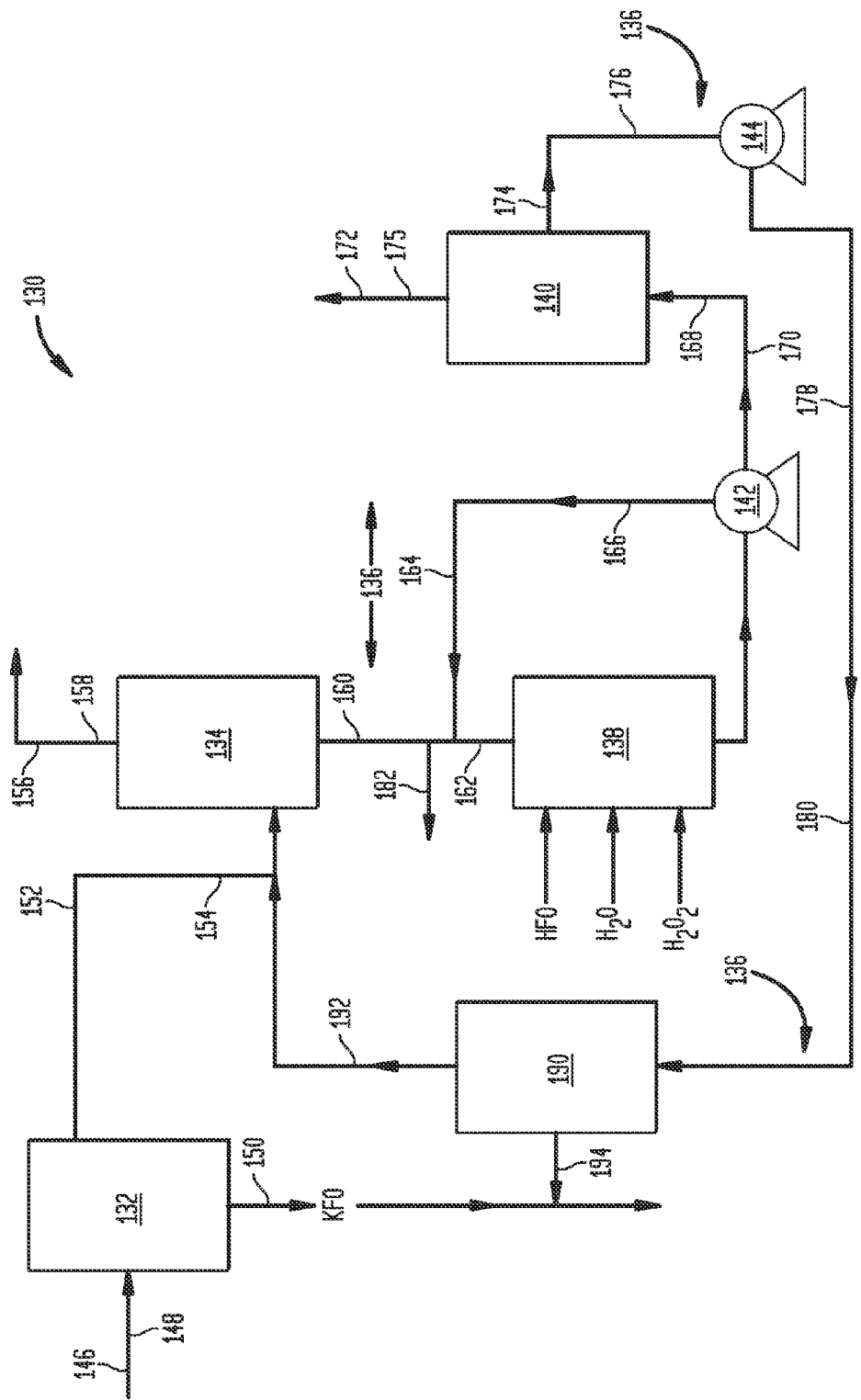
FIG. 3 is a simplified schematic diagram of another alcohol reclamation system of the invention integrated with a conventional product recovery system.

Another embodiment showing integration of the inventive recovery system is shown in FIG. 3 which provides a system 130 including a multistage water/ethyl acetate extraction system 132, a distillation tower 134 and a residue recovery recycle loop 136. Loop 136 includes a mixing system 138, a heated hydrolysis reactor 140, an extraction/neutralization unit 190 as well as pumps 142, 144 and a plurality of connecting conduits therebetween.

Extraction system 132 and purification tower 134 may be of conventional design as noted above in connection with FIG. 2 wherein a TMP/formate crude product stream 146 is fed to system 132 via line 148 where potassium formate is extracted in an aqueous phase and recovered as stream 150. TMP is recovered from system 132 in an organic phase 152 and fed to tower 134 via line 154 wherein TMP is taken together with light ends as an overhead stream 156 via line 158 and directed to further purification.

Distillation residue exits tower 134 as stream 160 and is fed to mixing system 138 via line 162. In mixing system 138 hydrogen peroxide, water and formic acid are added to the purification residue and the resulting mixture is partially recycled to system 138 as stream 164 via line 166 by way of pump 142. Any equivalent means of providing hydrogen peroxide, water and acid to the reaction mixture are also contemplated, for example, these components may be admixed before or provided directly to reactor 140.

Pump 142 also provides a reactant stream 168 including purification residue, formic acid and hydrogen peroxide to hydrolysis and oxidation reactor 140 via line 170. In reactor 140, TMP is recovered from stream 168 as described above in connection with Examples 1-13 and any excess $H_2O_2$ is vented to a scrubber as stream 172 via line 175.

Reactor 140 is a plug flow type overflow reactor. A reacted stream 174 is enriched in TMP by the alcohol recovery process of the invention and the liquor exits via line 176 to pump 144 which pumps the material as stream 178 via line 180 to extraction/neutralization unit 190 where formic acid in the effluent from reactor 140 is neutralized to potassium formate and exits the unit as stream 194 which is combined with stream 150. Reclaimed TMP exits unit 190 as an organic stream 192 which is combined with organic phase 152 and fed to tower 134.

The alcohol reclaimed from the purification residue is thus returned to an existing purification tower where it is recovered along with product from a fresh raw product stream.

As system 130 operates, levels of heavy by-products in stream 160 increase because of the operation of residue cycle loop 136 and are further processed or incinerated for steam generation as noted above in connection with FIG. 2. To this end, a purge stream 182 is drawn from stream 160 as shown.

There is thus provided in a first Embodiment, a method of reclaiming trimethylolpropane from purification residue comprising hydrolyzing a purification residue with an aqueous medium in the presence of (i) an acid and (ii) an oxidizing agent to reclaim trimethylolpropane from one or more TMP-formals selected from:

monocyclic TMP-formal (MCF); Formula I:

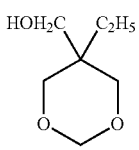
(I)

monolinear bis-TMP-formal (MBLF); Formula II:

(II)

Methyl-(monolinear)TMP-formal; Formula III

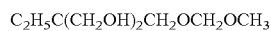
(III)

Methyl-(bislinear)TMP-formal; Formula IV

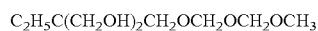
(IV)

and the cyclic formal of di-TMP; Formula V:

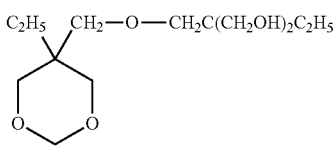
(V)

The following are additional embodiments:

Embodiment No. 2 is the method according to Embodiment No. 1, comprising hydrolyzing
monolinear bis-TMP-formal (MBLF); Formula II:

(II)

in the presence of (i) an acid and (ii) an oxidizing agent.

Embodiment No. 3 is the method according to Embodiment No. 1 or Embodiment No. 2, wherein said acid is selected from sulfuric acid, phosphoric acid, hydrochloric acid, sulfonic acid, organic acids or acid-functional ion exchange resin.

Embodiment No. 4 is the method according to Embodiment No. 1 and any or all of the other foregoing Embodiments, wherein said acid is formic acid.

Embodiment No. 5 is the method according to Embodiment No. 3, wherein said acid is an acid functional ion exchange resin.

Embodiment No. 6 is the method according to Embodiment No. 5, wherein said ion exchange resin is a sulfonic acid functional ion exchange resin.

Embodiment No. 7 is the method according to Embodiment No. 1 and any or all of the other foregoing Embodiments, wherein the hydrolysis reaction is carried out at a pH of less than 4.

Embodiment No. 8 is the method according to Embodiment Nos. 1 through 6, wherein the hydrolysis reaction is carried out at a pH of from 1 to 4.

Embodiment No. 9 is the method according to Embodiment No. 8, wherein the hydrolysis reaction is carried out at a pH of from 1.5 to 3.

Embodiment No. 10 is the method according to Embodiment No. 1 and any or all of the other foregoing Embodiments, further comprising neutralizing said aqueous medium with a neutralizing agent.

Embodiment No. 11 is the method according to Embodiment No. 10 wherein said acid is formic acid and said neutralizing agent is an alkali metal hydroxide.

Embodiment No. 12 is the method according to Embodiment No. 1 and any or all of the other foregoing Embodiments, effective to reclaim at least 75% by weight of the trimethylolpropane present in the trimethylolpropane formals of the purification residue.

Embodiment No. 13 is the method according to Embodiment No. 1 and any or all of the other foregoing Embodiments, effective to reclaim at least 80% by weight of the trimethylolpropane present in the trimethylolpropane formals of the purification residue.

Embodiment No. 14 is the method according to Embodiment No. 1 and any or all of the other foregoing Embodiments, effective to reclaim at least 85% by weight of the trimethylolpropane present in the trimethylolpropane formals of the purification residue.

Embodiment No. 15 is the method according to Embodiment No. 1 and any or all of the other foregoing Embodiments, effective to reclaim at least 90% by weight of the trimethylolpropane present in the trimethylolpropane formals of the purification residue.

Embodiment No. 16 is the method according to Embodiment No. 1 and any or all of the other foregoing Embodiments, wherein the oxidizing agent is supplied to the hydrolysis reaction in an amount of from 2 wt % to 40 wt % based on the dry weight of the purification residue.

Embodiment No. 17 is the method according to Embodiment No. 1 and any or all of the other foregoing Embodiments, wherein the oxidizing agent is supplied to the hydrolysis reaction in an amount of from 4 wt % to 20 wt % based on the dry weight of the purification residue.

Embodiment No. 18 is the method according to Embodiment No. 17, wherein the oxidizing agent is supplied to the hydrolysis reaction in an amount of from 5 wt % to 10 wt % based on the dry weight of the purification residue.

Embodiment No. 19 is the method according to Embodiment No. 1 and any or all of the other foregoing Embodiments, wherein the acid is supplied to the aqueous reaction medium in an amount of from 0.5 wt % to 20 wt % based on the total weight of the aqueous medium.

Embodiment No. 20 is the method according to Embodiment No. 19, wherein the acid is supplied to the aqueous reaction medium in an amount of from 1 wt % to 15 wt % based on the total weight of the aqueous medium.

Embodiment No. 21 is the method according to Embodiment No. 20, wherein the acid is supplied to the aqueous reaction medium in an amount of from 2 wt % to 10 wt % based on the total weight of the aqueous medium.

Embodiment No. 22 is the method according to Embodiment No. 1 and any or all of the other foregoing Embodiments, wherein water is supplied to the reaction medium in a weight ratio of water:organic mixture from 0.5 W/W to 4 W/W.

Embodiment No. 23 is the method according to Embodiment No. 22, wherein water is supplied to the reaction medium in a weight ratio of water:organic mixture from 1 W/W to 3 W/W.

Embodiment No. 24 is the method according to Embodiment No. 23, wherein water is supplied to the reaction medium in a weight ratio of water:organic mixture from 1.5 W/W to 2.5 W/W.

Embodiment No. 25 is the method according to Embodiment No. 1 and any or all of the other foregoing Embodiments, wherein the hydrolysis temperature is maintained within the range of from 50° C. to 99° C.

Embodiment No. 26 is the method according to Embodiment No. 25, wherein the hydrolysis temperature is maintained within the range of from 70° C. to 95° C.

Embodiment No. 27 is the method according to Embodiment No. 1 and any or all of the other foregoing Embodiments, wherein the hydrolysis reaction is carried out for a reaction period of from about 0.5 hours to about 10 hours.

Embodiment No. 28 is the method according to Embodiment No. 27, wherein the hydrolysis reaction is carried out for a reaction period of from about 1 hour to about 7.5 hours.

Embodiment No. 29 is the method according to Embodiment No. 28, wherein the hydrolysis reaction is carried out for a reaction period of from about 1.5 hours to about 4.5 hours.

Embodiment No. 30 is the method according to Embodiment No. 1 and any or all of the other foregoing Embodiments, wherein reactants, temperature and reaction time are selected such that the yield of trimethylolpropane is from 50% to 99% based on the weight of TMP-formal derivate in the purification residue.

Embodiment No. 31 is the method according to Embodiment No. 30, wherein reactants, temperature and reaction time are selected such that the yield of trimethylolpropane is from 60% to 98% based on the weight of TMP-formal derivate in the purification residue.

Embodiment No. 32 is the method according to Embodiment No. 30, wherein reactants, temperature and reaction time are selected such that the yield of trimethylolpropane is from 75% to 95% based on the weight of TMP-formal derivate in the purification residue.

Embodiment No. 33 is the method according to Embodiment No. 32, wherein reactants, temperature and reaction time are selected such that the yield of trimethylolpropane is greater than 80% based on the weight of TMP formal derivate in the purification residue.

Embodiment No. 34 is a process for reclaiming trimethylolpropane from purification residue comprising: (a) continuously feeding a purification residue stream to a reaction vessel, said purification residue stream containing one or more trimethylolpropane formals selected from:
monocyclic TMP-formal (MCF); Formula I:

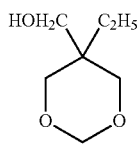

(I)

monolinear bis-TMP-formal (MBLF); Formula II:

$$[C_2H_5C(CH_2OH)_2CH_2O]_2CH_2 \qquad (II)$$

Methyl-(monolinear)TMP-formal; Formula III $$C_2H_5C(CH_2OH)_2CH_2OCH_2OCH_3 \qquad (III)$$

Methyl-(bislinear)TMP-formal; Formula IV $$C_2H_5C(CH_2OH)_2CH_2OCH_2OCH_2OCH_3 \qquad (IV)$$

and formal of di-TMP; the cyclic Formula V:

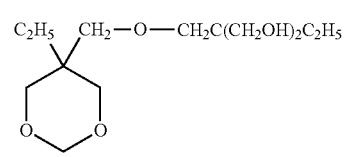

(V)

(b) providing water, an acid and an oxidizing agent to the reaction vessel such that a reaction mixture including the purification residue, water, acid and oxidizing agent is formed; (c) maintaining the reaction mixture in the reaction vessel at a time and temperature such that one or more of said TMP-formals are hydrolyzed to thereby enrich the reaction mixture with reclaimed trimethylolpropane; and (d) continuously withdrawing a reclaimed trimethylolpropane stream from the reaction vessel. This embodiment many utilize any of, or all of, the features of Embodiments 1-33.

Embodiment No. 35 is the process according to Embodiment No. 34, wherein the reclaimed trimethylolpropane stream from step (d) is subjected to a distillation to obtain trimethylolpropane containing light ends and a distillation residue.

Embodiment No. 36 is the method according to Embodiment No. 35, wherein the reclaimed trimethylolpropane stream is combined with another trimethylolpropane stream to provide a combined trimethylolpropane stream prior to distillation.

Embodiment No. 37 is the method according to Embodiment No. 36, wherein formate is extracted from the combined trimethylolpropane stream prior to distillation.

Embodiment No. 38 is a process for purifying a trimethylolpropane containing stream comprising: (a) distilling a trimethylolpropane containing stream to provide an overhead product stream and a purification residue stream; (b) feeding the purification residue stream to a reaction vessel, said purification residue stream containing one or more trimethylolpropane formals selected from:
monocyclic TMP-formal (MCF); Formula I:

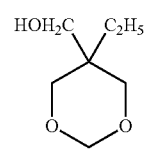

(I)

monolinear bis-TMP-formal (MBLF); Formula II:

$$[C_2H_5C(CH_2OH)_2CH_2O]_2CH_2 \qquad (II)$$

Methyl-(monolinear)TMP-formal; Formula III $$C_2H_5C(CH_2OH)_2CH_2OCH_2OCH_3 \qquad (III)$$

Methyl-(bislinear)TMP-formal; Formula IV

and formal of di-TMP; the cyclic Formula V:

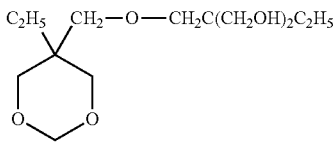

(c) continuously providing water, an acid and an oxidizing agent to the reaction vessel such that a reaction mixture including the purification residue, water, acid and oxidizing agent is formed; (d) maintaining the reaction mixture in the reaction vessel at a time and temperature such that one or more of said trimethylol formals are hydrolyzed to thereby enrich the reaction mixture with reclaimed trimethylolpropane; (e) withdrawing a reclaimed trimethylolpropane stream from the reaction vessel; and (f) recycling reclaimed trimethylolpropane to step (a). This embodiment many utilize any of, or all of the features of Embodiments 1-37.

Embodiment No. 39 is the method according to Embodiment No. 38, wherein an aqueous phase is extracted from the reclaimed trimethylolpropane stream prior to recycling reclaimed trimethylolpropane to step (a).

Embodiment No. 40 is a purification system for recovering trimethylolpropane from a raw product stream comprising trimethylolpropane and formate comprising: (a) an extraction system adapted to receive the raw product stream and provide aqueous output containing formate and an organic output containing trimethylolpropane; (b) a distillation tower adapted to receive organic output of the extraction system and provide trimethylolpropane and light ends as overhead and purification residue, wherein the purification residue contains one or more TMP-formals selected from:

monocyclic TMP-formal (MCF); Formula I:

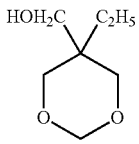

monolinear bis-TMP-formal (MBLF); Formula II:

Methyl-(monolinear)TMP-formal; Formula III

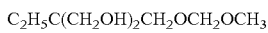

Methyl-(bislinear)TMP-formal; Formula IV

and the cyclic formal of di-TMP; Formula V:

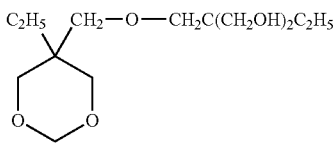

(c) means for providing water, an oxidizing agent, and acid to the purification residue to provide an aqueous residue mixture; (d) a reactor adapted for receiving the aqueous residue mixture and maintaining the reaction mixture in the reaction vessel at a time and temperature such that one or more of said TMP-formals are hydrolyzed to thereby enrich the reaction mixture with reclaimed trimethylolpropane; and (e) a recycle system for recycling reclaimed trimethylolpropane from the reactor vessel to the extraction system of part (a) or for recycling reclaimed trimethylolpropane from the reactor to the distillation tower of part (b). Any of, or all of the features of Embodiments 1-39 may be employed in connection with the system of this embodiment.

While the invention has been described in detail, modifications within the spirit and scope of the invention will be readily apparent to those of skill in the art. Such modifications are also to be considered as part of the present invention. In view of the foregoing discussion, relevant knowledge in the art and references discussed above in connection with the Background of the Invention, the Summary of Invention and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A method of reclaiming trimethylolpropane from purification residue comprising hydrolyzing a purification residue with an aqueous medium in the presence of (i) an acid and (ii) an oxidizing agent to reclaim trimethylolpropane from one or more TMP-formals selected from:

monocyclic TMP-formal (MCF); Formula I:

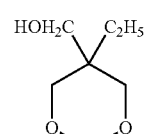

monolinear bis-TMP-formal (MBLF); Formula II:

Methyl-(monolinear)TMP-formal; Formula III

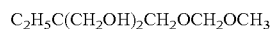

Methyl-(bislinear)TMP-formal; Formula IV

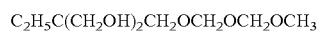

and the cyclic formal of di-TMP; Formula V:

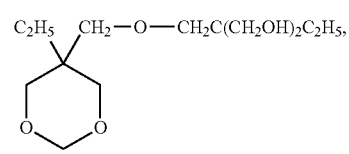

wherein the hydrolysis reaction is carried out at a pH of from 1 to 4 and wherein the oxidizing agent is supplied to the hydrolysis reaction in an amount of from 2 wt % to 40 wt % based on the dry weight of the purification residue.

2. The method according to claim 1, comprising hydrolyzing monolinear bis-TMP-formal (MBLF); Formula II:

3. The method according to claim 1, wherein said acid is selected from sulfuric acid, phosphoric acid, hydrochloric acid, sulfonic acid, organic acids or acid-functional ion exchange resin.

4. The method according to claim 1, wherein said acid is formic acid.

5. The method according to claim 1, wherein said acid is an acid functional ion exchange resin.

6. The method according to claim 1, further comprising neutralizing said aqueous medium with a neutralizing agent.

7. The method according to claim 1, effective to reclaim at least 85% by weight of the trimethylolpropane present in the trimethylolpropane formals of the purification residue.

8. The method according to claim 1, wherein the acid is supplied to the aqueous reaction medium in an amount of from 0.5 wt % to 20 wt % based on the total weight of the aqueous medium.

9. The method according to claim 1, wherein water is supplied to the reaction medium in a weight ratio of water:organic mixture from 1 W/W to 3 W/W.

10. The method according to claim 1, wherein the hydrolysis temperature is maintained within the range of from 70° C. to 95° C.

11. The method according to claim 1, wherein the hydrolysis reaction is carried out for a reaction period of from about 1 hour to about 7.5 hours.

12. The method according to claim 1, wherein reactants, temperature and reaction time are selected such that the yield of trimethylolpropane is from 75% to 95% based on the weight of TMP-formal derivate in the purification residue.

13. A process for reclaiming trimethylolpropane from purification residue comprising:
(a) continuously feeding a purification residue stream to a reaction vessel, said purification residue stream containing one or more trimethylolpropane formals selected from:
monocyclic TMP-formal (MCF); Formula I:

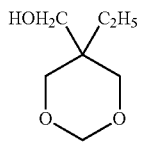
(I)

monolinear bis-TMP-formal (MBLF); Formula II:

[C$_2$H$_5$C(CH$_2$OH)$_2$CH$_2$O]$_2$CH$_2$ (II)

Methyl-(monolinear)TMP-formal; Formula III

C$_2$H$_5$C(CH$_2$OH)$_2$CH$_2$OCH$_2$OCH$_3$ (III)

Methyl-(bislinear)TMP-formal; Formula IV

C$_2$H$_5$C(CH$_2$OH)$_2$CH$_2$OCH$_2$OCH$_2$OCH$_3$ (IV)

and formal of di-TMP; the cyclic Formula V:

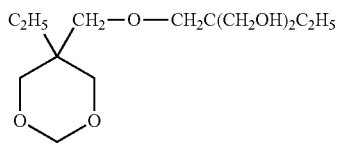
(V)

(b) providing water, an acid and an oxidizing agent to the reaction vessel such that a reaction mixture including the purification residue, water, acid and oxidizing agent is formed;

(c) maintaining the reaction mixture in the reaction vessel at a time and temperature such that one or more of said TMP-formals are hydrolyzed to thereby enrich the reaction mixture with reclaimed trimethylolpropane, wherein the hydrolysis reaction is carried out at a pH of from 1 to 4 and wherein the oxidizing agent is supplied to the hydrolysis reaction in an amount of from 2 wt % to 40 wt % based on the dry weight of the purification residue; and (d) continuously withdrawing a reclaimed trimethylolpropane stream from the reaction vessel.

14. The process according to claim 13, wherein the reclaimed trimethylolpropane stream from step (d) is subjected to a distillation to obtain trimethylolpropane containing light ends and a distillation residue.

15. The method according to claim 14, wherein the reclaimed trimethylolpropane stream is combined with another trimethylolpropane stream to provide a combined trimethylolpropane stream prior to distillation.

16. The method according to claim 15, wherein formate is extracted from the combined trimethylolpropane stream prior to distillation.

17. A process for purifying a trimethylolpropane containing stream comprising:
(a) distilling a trimethylolpropane containing stream to provide an overhead product stream and a purification residue stream;
(b) feeding the purification residue stream to a reaction vessel, said purification residue stream containing one or more trimethylolpropane formals selected from:
monocyclic TMP-formal (MCF); Formula I:

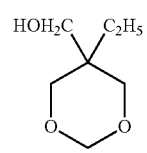
(I)

monolinear bis-TMP-formal (MBLF); Formula II:

[C$_2$H$_5$C(CH$_2$OH)$_2$CH$_2$O]$_2$CH$_2$ (II)

Methyl-(monolinear)TMP-formal; Formula III

C$_2$H$_5$C(CH$_2$OH)$_2$CH$_2$OCH$_2$OCH$_3$ (III)

Methyl-(bislinear)TMP-formal; Formula IV

C$_2$H$_5$C(CH$_2$OH)$_2$CH$_2$OCH$_2$OCH$_2$OCH$_3$ (IV)

and formal of di-TMP; the cyclic Formula V:

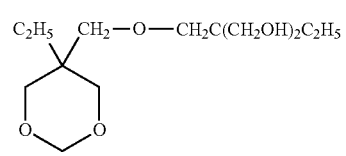
(V)

(c) continuously providing water, an acid and an oxidizing agent to the reaction vessel such that a reaction mixture including the purification residue, water, acid and oxidizing agent is formed;

(d) maintaining the reaction mixture in the reaction vessel at a time and temperature such that one or more of said trimethylol formals are hydrolyzed to thereby enrich the reaction mixture with reclaimed trimethylolpropane, wherein the hydrolysis reaction is carried out at a pH of from 1 to 4 and wherein the oxidizing agent is supplied to the hydrolysis reaction in an amount of from 2 wt % to 40 wt % based on the dry weight of the purification residue;

(e) withdrawing a reclaimed trimethylolpropane stream from the reaction vessel; and (f) recycling reclaimed trimethylolpropane to step (a).

18. A purification system for recovering trimethylolpropane from a raw product stream comprising trimethylolpropane and formate comprising:

(a) an extraction system adapted to receive the raw product stream and provide aqueous output containing formate and an organic output containing trimethylolpropane;

(b) a distillation tower adapted to receive organic output of the extraction system and provide trimethylolpropane and light ends as overhead and purification residue, wherein the purification residue contains one or more TMP-formals selected from:

monocyclic TMP-formal (MCF); Formula I:

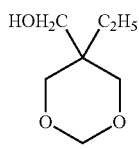
(I)

monolinear bis-TMP-formal (MBLF); Formula II:

(II)

Methyl-(monolinear)TMP-formal; Formula III

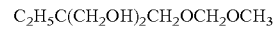
(III)

Methyl-(bislinear)TMP-formal; Formula IV

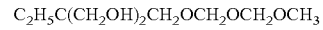
(IV)

and formal of di-TMP; the cyclic Formula V:

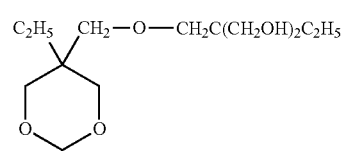
(V)

(c) means for providing water, an oxidizing agent, and acid to the purification residue to provide an aqueous residue mixture;

(d) a reactor adapted for receiving the aqueous residue mixture and maintaining the reaction mixture in the reaction vessel at a time and temperature such that one or more of said TMP-formals are hydrolyzed to thereby enrich the reaction mixture with reclaimed trimethylolpropane, wherein the hydrolysis reaction is carried out at a pH of from 1 to 4 and wherein the oxidizing agent is supplied to the hydrolysis reaction in an amount of from 2 wt % to 40 wt % based on the dry weight of the purification residue; and (e) a recycle system for recycling reclaimed trimethylolpropane from the reactor vessel to the extraction system of part (a) or for recycling reclaimed trimethylolpropane from the reactor to the distillation tower of part (b).

* * * * *